United States Patent
Takizawa et al.

(10) Patent No.: US 9,753,281 B2
(45) Date of Patent: Sep. 5, 2017

(54) SCANNING ENDOSCOPE WITH LONGITUDINAL VIBRATION ABSORPTION

(71) Applicant: OLYMPUS CORPORATION, Tokyo (JP)

(72) Inventors: Hiroyuki Takizawa, Chofu (JP); Yuji Sakai, Kodaira (JP); Daiki Ariyoshi, Chofu (JP); Soichiro Koshika, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/270,572

(22) Filed: Sep. 20, 2016

(65) Prior Publication Data
US 2017/0010460 A1   Jan. 12, 2017

Related U.S. Application Data

(63) Continuation of application No. PCT/JP2015/074878, filed on Sep. 1, 2015.

(30) Foreign Application Priority Data

Nov. 20, 2014   (JP) .................................. 2014-235726

(51) Int. Cl.
*G02B 26/10*   (2006.01)
*A61B 1/00*   (2006.01)
(Continued)

(52) U.S. Cl.
CPC ........ *G02B 26/103* (2013.01); *A61B 1/00045* (2013.01); *A61B 1/0051* (2013.01);
(Continued)

(58) Field of Classification Search
None
See application file for complete search history.

(56) References Cited

U.S. PATENT DOCUMENTS

| 2010/0274082 A1* | 10/2010 | Iguchi | A61B 1/0005 600/109 |
| 2014/0300901 A1* | 10/2014 | Cha | G01B 9/0205 356/479 |

(Continued)

FOREIGN PATENT DOCUMENTS

| JP | 2011-139781 A | 7/2011 |
| JP | 2012-078733 A | 4/2012 |
| JP | 2013-244045 A | 12/2013 |

OTHER PUBLICATIONS

International Search Report issued in PCT/JP2015/074878 dated Nov. 2, 2015.

*Primary Examiner* — Mike Stahl
(74) *Attorney, Agent, or Firm* — Scully, Scott, Murphy & Presser, P.C.

(57) ABSTRACT

A scanning endoscope includes: an optical fiber that guides light emitted from a light source section, and emits the light from a distal end; an actuator that expands and contracts to scan with the light emitted from the distal end of the optical fiber; a ferrule that transmits, to the optical fiber, force corresponding to the expansion and contraction of the actuator; a ferrule holding part that holds the ferrule; a lens holding part that is formed of a cylindrical member provided outside the optical fiber along the optical fiber, and holds a lens, the lens receiving the light emitted from the distal end of the optical fiber; and an absorption part that absorbs vibration, in a longitudinal direction of the cylindrical member, of at least one of the ferrule holding part and the lens holding part.

8 Claims, 7 Drawing Sheets

(51) Int. Cl.
    *A61B 1/005*     (2006.01)
    *A61B 1/06*     (2006.01)
    *G02B 23/24*     (2006.01)
    *A61B 5/00*     (2006.01)
    *A61B 1/07*     (2006.01)
    *H04N 5/225*     (2006.01)

(52) U.S. Cl.
    CPC ...... *A61B 1/00078* (2013.01); *A61B 1/00172* (2013.01); *A61B 1/0669* (2013.01); *A61B 5/0059* (2013.01); *G02B 23/2469* (2013.01); *A61B 1/0638* (2013.01); *A61B 1/07* (2013.01); *H04N 2005/2255* (2013.01)

(56) References Cited

U.S. PATENT DOCUMENTS

2015/0374219 A1* 12/2015 Yoshino ............. A61B 1/00133
                                                    600/137
2016/0216510 A1* 7/2016 Tsuruta ................ G01N 21/474

* cited by examiner

SCANNING ENDOSCOPE WITH LONGITUDINAL VIBRATION ABSORPTION

CROSS REFERENCE TO RELATED APPLICATION

This application is a continuation application of PCT/JP2015/074878 filed on Sep. 1, 2015 and claims benefit of Japanese Application No. 2014-235726 filed in Japan on Nov. 20, 2014, the entire contents of which are incorporated herein by this reference.

BACKGROUND OF THE INVENTION

1. Field of the Invention

The present invention relates to a scanning endoscope that scans with illuminating light to acquire an endoscope image.

2. Description of the Related Art

In recent years, an endoscope that scans with illuminating light has been widely used in a medical field and other fields. In addition, a scanning endoscope that two-dimensionally scans an object such as a site to be observed, with light guided by an optical fiber and receives light reflected from the object to form an image is also proposed.

For example, a conventional example of Japanese Patent Application Laid-Open Publication No. 2012-78733 discloses a scanning confocal endoscope apparatus in which laser light emitted from an optical fiber that serves as a guide member swung (moved) by an actuator is condensed by a lens unit. In the conventional example, an inner cylinder that has a distal end fixed with the lens unit and a middle part fixed with a mount holding an actuator is slidably disposed with respect to an outer cylinder. The inner cylinder is moved in a Z-axis direction by a Z-axis actuator that is disposed on proximal end side of the inner cylinder. As for a member holding the Z-axis actuator, a configuration in which a part of an outer periphery is cut out and fixed (connected) to the outer cylinder has been disclosed.

SUMMARY OF THE INVENTION

A scanning endoscope according to an aspect of the present invention includes: an optical fiber that guides light emitted from a light source section, and emits the light from a distal end; an actuator that expands and contracts in response to a provided voltage to scan with the light emitted from the distal end of the optical fiber; a ferrule that is interposed between the optical fiber and the actuator, and transmits, to the optical fiber, force corresponding to the expansion and contraction of the actuator; a ferrule holding part that is connected to the ferrule to hold the ferrule; a lens holding part that has a space containing the optical fiber, is formed of a cylindrical member provided outside the optical fiber along the optical fiber, and holds a lens, the lens receiving the light emitted from the distal end of the optical fiber and emitting illuminating light to an object; and an absorption part that is provided between the ferrule holding part and the lens holding part, and absorbs or suppresses vibration, in a longitudinal direction of the cylindrical member, of at least one of the ferrule holding part and the lens holding part.

DETAILED DESCRIPTION OF THE PREFERRED EMBODIMENT

Hereinafter, an embodiment of the present invention is described with reference to drawings.

Figure 1:
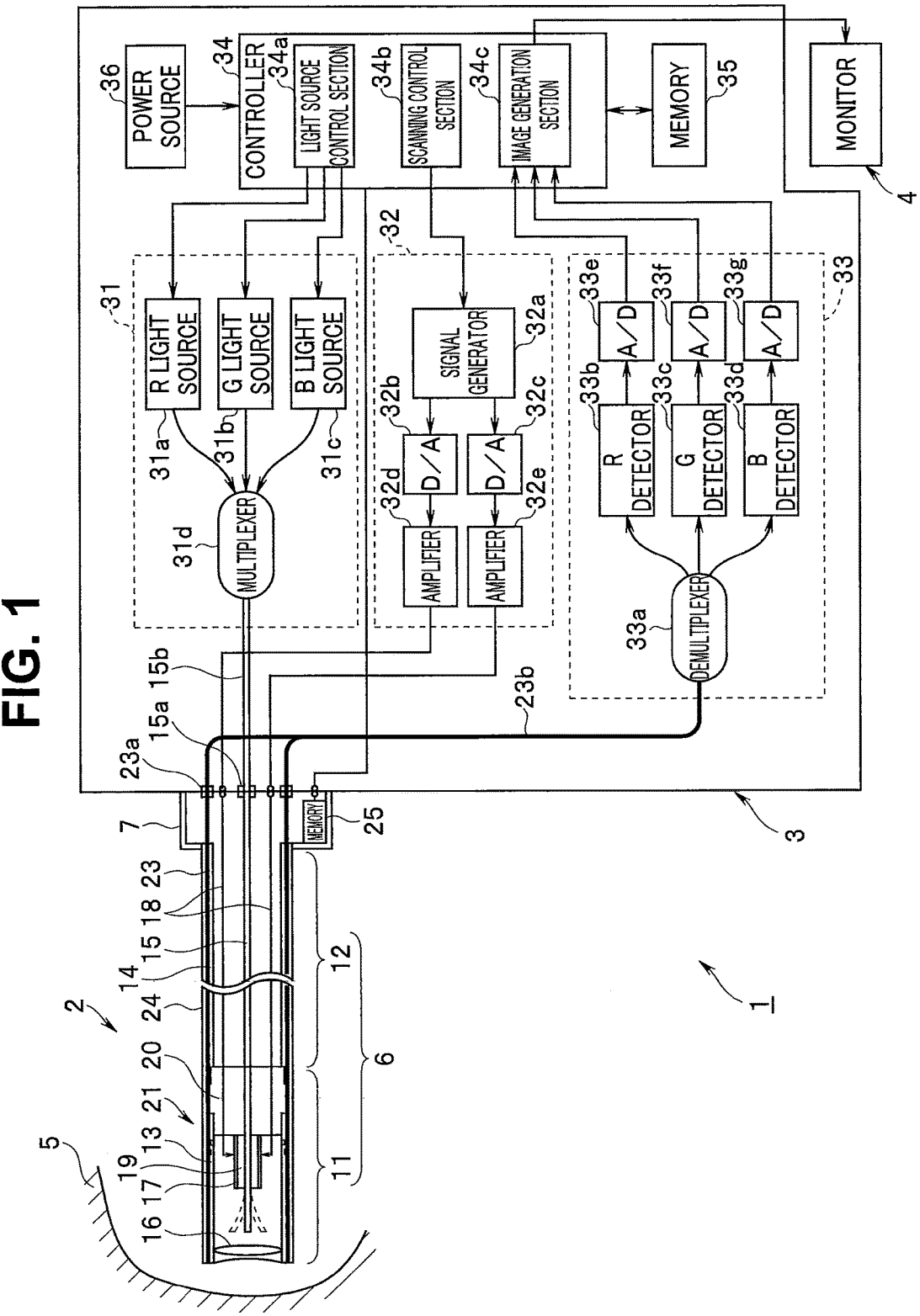
FIG. 1 is a diagram illustrating an entire configuration of a scanning endoscope apparatus including an embodiment of the present invention.

As illustrated in FIG. 1, a scanning endoscope apparatus 1 includes: a scanning endoscope 2 of the embodiment of the present invention; a main body device (or a scanning endoscope control device) 3 to which the scanning endoscope 2 is detachably connected; and a monitor 4 serving as a display unit connected to the main body device 3.

The scanning endoscope 2 includes a flexible insertion portion 6 that is formed in an elongated shape insertable into a body or a body cavity of a subject 5. A connector 7 that detachably connects the scanning endoscope 2 to the main body device 3 is provided at a proximal end (a rear end) of the insertion portion 6.

Also, the insertion portion 6 includes a rigid distal end portion 11 and a flexible tube part 12 that extends from a rear end of the distal end portion 11 to the connector 7. Note that a bendable bending portion may be provided between the distal end portion 11 and the flexible tube part 12, and an operation section including an operation knob or the like that causes the bending portion to bend may be provided between the flexible tube part 12 and the connector 7.

The distal end portion 11 includes the cylindrical member 13 serving as a rigid cylindrical member. A distal end of a flexible cylindrical tube 14 is coupled with a rear end of the cylindrical member 13, and a rear end of the cylindrical tube 14 is fixed to the connector 7.

An optical fiber 15 that forms a light guide member guiding illuminating light is inserted into the insertion portion 6, and a proximal end (a rear end) of the optical fiber 15 is connected to an optical fiber 15b inside the main body device 3 at an optical connection part 15a of the connector 7. The illuminating light generated by a light source unit 31 inside the main body device 3 enters the proximal end of the optical fiber 15 through the optical fiber 15b. The illuminating light guided by the optical fiber 15 is emitted from a distal end surface of the optical fiber 15 toward an object such as an examination site in the subject 5 through a condensing illumination lens 16 that is so attached at a distal end of the cylindrical member 13 as to face the distal end surface of the optical fiber 15.

Figure 2:
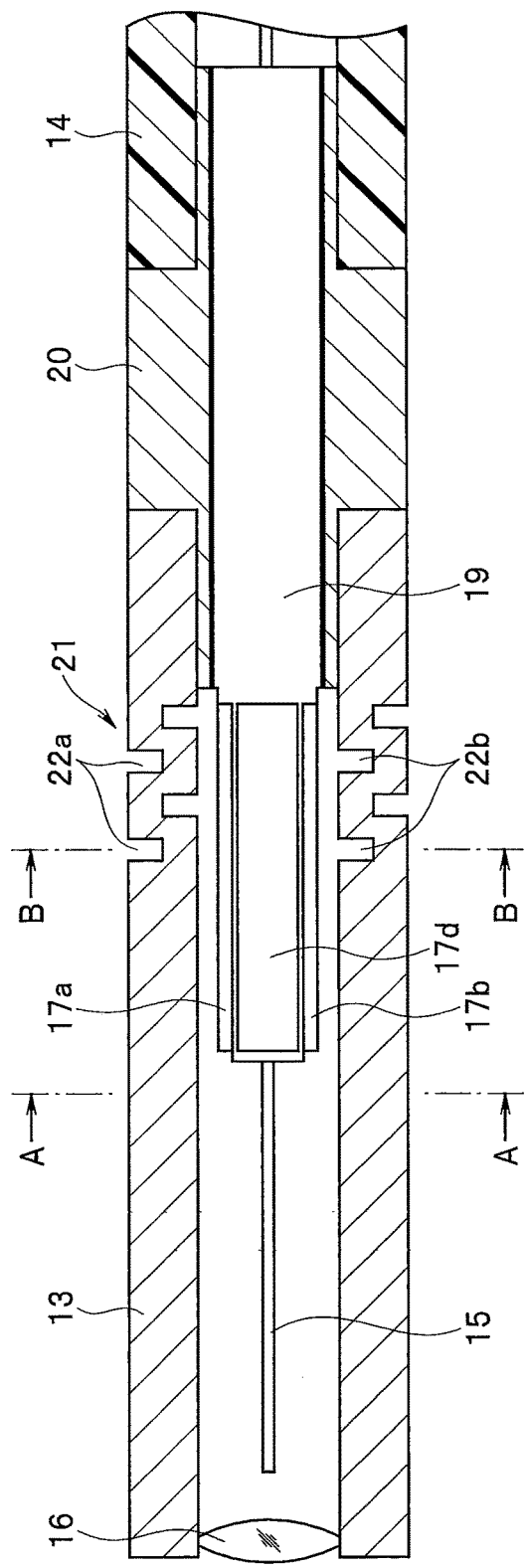
FIG. 2 is a longitudinal sectional view illustrating a configuration inside a cylindrical member of a scanning endoscope of the embodiment.

As illustrated also in FIG. 2, an actuator 17 is disposed inside the cylindrical member 13 that forms the distal end portion 11. The actuator 17 forms a driving section that drives to swing the distal end side of the optical fiber 15 in a direction orthogonal to a longitudinal direction of the optical fiber 15. The actuator 17 expands and contracts in response to a drive signal that is applied from a driving unit 32 inside the main body device 3 through a driving line 18. The driving line 18 is inserted into the insertion portion 6.

The actuator 17 is joined by a ferrule 19 that serves as a joining member interposed between the optical fiber 15 and the actuator 17. The ferrule 19 transmits force corresponding to expansion and contraction of the actuator 17 to the optical fiber 15.

A proximal end (a rear end) side of the ferrule 19 is held by a ferrule holding member 20 that forms a ferrule holding part holding the ferrule 19.

Also, in the present embodiment, an absorption part 21 that absorbs or suppresses vibration of the cylindrical member 13 in a longitudinal direction (namely, vertical vibration) is provided, for example, at a position close to the proximal end in the longitudinal direction of the cylindrical member 13, namely, at a position close to the ferrule holding member 20.

Figure 3A:
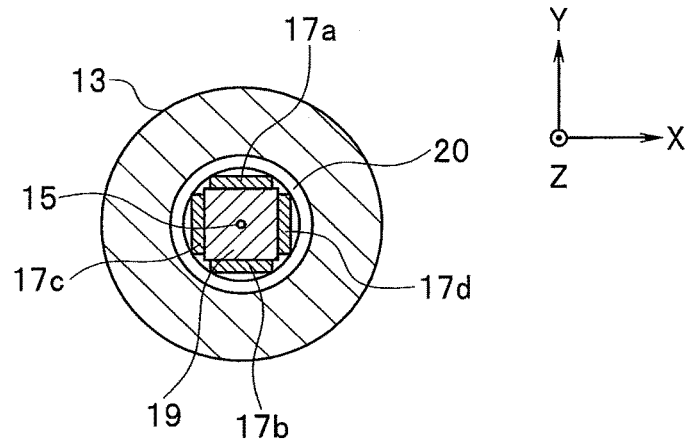
FIG. 3A is a sectional view taken along line A-A in FIG. 2.

As illustrated in FIG. 2 and FIG. 3, the ferrule 19 serving as a rigid joining member that has a rectangular parallelepiped shape in the longitudinal direction inside the cylindrical member 13 may be formed of, for example, zirconia (ceramic) or nickel.

The ferrule 19 is so formed as to have a square prism shape as illustrated in a lateral cross section of FIG. 3, and the optical fiber 15 is fixed to the ferrule 19 along a central axis. Actuator elements 17a and 17b are attached to both side surfaces of the ferrule 19 in a Y-axis direction (the vertical direction of a paper surface), and actuator elements 17c and 17d are attached to both side surfaces of the ferrule 19 in an X-axis direction (the lateral direction of the paper surface).

Each of the actuator elements may be formed of, for example, a piezoelectric element, and expands and contracts in the longitudinal direction (in the Z-axis direction in FIG. 3) in response to application of a drive signal. Therefore, for example, drive signals with inverted phases are applied to the actuator elements 17a and 17b (to cause one of the actuator elements 17a and 17b to expand and cause the other to contract) while proximal ends of the respective actuator elements 17a and 17b are held or fixed, which makes it possible to swing the distal end side of the optical fiber 15 in the vertical direction as illustrated by a dashed line in FIG. 1.

Also, the proximal end side of the ferrule holding member 20 is engaged with the proximal end of the cylindrical member 13 and is fixed with an adhesive or the like.

Further, as illustrated in FIG. 2, the absorption part (or a suppression part) 21 is provided in an outer circumferential face and an inner circumferential face that are close to the proximal end of the cylindrical member 13. The absorption part (or the suppression part) 21 that absorbs or suppresses vibration of the cylindrical member 13 in the longitudinal direction is formed by cutouts 22a and 22b formed in a circumferential direction. The absorption part 21 is described in more detail later.

As illustrated in FIG. 1, a plurality of light-receiving optical fibers 23 are arranged in a ring form along the outer circumferential face of the cylindrical member 13 and the cylindrical tube 14. The light-receiving optical fibers 23 receive illuminating light that has been reflected by the object. The light that has been received by the light-receiving optical fibers 23 (the returned light or the reflected light from the object) is guided to a light-receiving optical fiber 23b inside the main body device 3 through an optical connection part 23a of the connector 7. The light guided by the light-receiving optical fiber 23b enters a detection unit 33 and is then converted into an electric signal.

The light-receiving optical fibers 23 arranged in a ring form are covered with and protected by an exterior member 24.

Also, the scanning endoscope 2 includes a memory 25. The memory 25 stores information such as drive data that allows the actuator 17 to drive the distal end of the optical fiber 15 along a predetermined scanning pattern, and coordinate position data corresponding to an irradiation position when the distal end of the optical fiber 15 is driven. The information stored by the memory 25 is provided to a controller 34 inside the main body device 3 through a contact of the connector 7 and a signal line.

The main body device 3 includes: the light source unit 31; the driving unit 32; the detection unit 33; the controller 34 that controls each unit in the main body device 3; a memory 35 that is connected to the controller 34 and stores various kinds of information; and a power supply (circuit) 36 that supplies DC power to the controller 34 and other components.

The light source unit 31 includes: a red (R) light source 31a that generates light of red wavelength band (also referred to as R light); a green (G) light source 31b that generates light of green wavelength band (also referred to as G light); a blue (B) light source 31c that generates light of blue wavelength band (also referred to as B light); and a multiplexer 31d that multiplexes (mixes) R light, light, and B light.

The R light source 31a, the G light source 31b, and the B light source 31c may be each configured by using, for example, a laser light source, and respectively emit R light, G light, and B light to the multiplexer 31d when being turned on through the control of the controller 34. The controller 34 includes a light source control section 34a that controls discrete light emission of the R light source 31a, the G light source 31b, and the B light source 31c. The light source control section 34a may be configured of, for example, a central processing unit (abbreviated as CPU).

The light source control section 34a of the controller 34 transmits, to the R light source 31a, the G light source 31b, and the B light source 31c, a control signal that causes the respective light sources to concurrently perform pulse light emission. The R light source 31a, the G light source 31b, and the B light source 31c concurrently generate and emit R light, G light, and B light, respectively, toward the multiplexer 31d.

The multiplexer 31d multiplexes the R light from the R light source 31a, the G light from the G light source 31b, and the B light from the B light source 31c, and supplies the multiplexed light to a light entering surface of the optical fiber 15b. The optical fiber 15b supplies the multiplexed light of the R light, the G light, and the B light to the optical fiber 15 as illuminating light.

The driving unit 32 includes a signal generator 32a, D/A converters 32b and 32c, and amplifiers 32d and 32e.

The signal generator 32a generates, based on the control of a scanning control section 34b of the controller 34, a drive signal to move (or to swing) a light emitting end part of the distal end of the optical fiber 15, and provides the drive signal to the D/A converters 32b and 32c, The D/A converters 32b and 32c convert the digital drive signal provided from the signal generator 32a into an analog drive signal, and respectively provide the analog drive signal to the amplifier 32d and 32e.

Figure 4A:
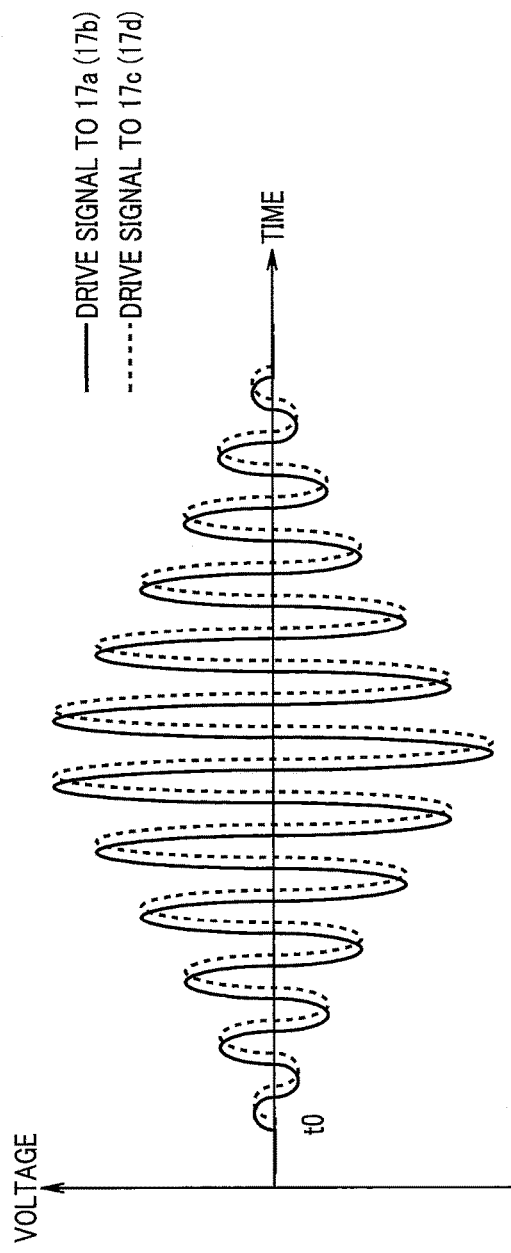
FIG. 4A is a diagram illustrating waveforms of drive signals that drive an actuator.

The amplifiers 32d and 32e amplify the drive signals that are respectively provided from the D/A converters 32b and 32c, and provide, to the actuator 17, the amplified drive signals that have waveforms illustrated in FIG. 4A.

Figure 4B:
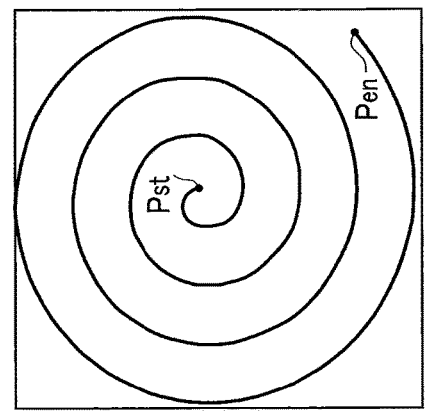
FIG. 4B is a diagram illustrating trajectory on which a distal end of an optical fiber is swung by the drive signal of FIG. 4A.

Then, the distal end of the optical fiber 15 is so swung as to form spiral-shaped scanning trajectory illustrated in FIG. 4B.

The detection unit 33 includes a demultiplexer 33a, detectors 33b, 33c, and 33d, and A/D converters 33e, 33f, and 33g.

The demultiplexer 33a includes a dichroic mirror or the like, and separates the returned light that has been emitted from the light emitting end surface of the light-receiving optical fiber 23b, into light of color components of R (red), G (green), and B (blue), and emits the light of the color components respectively to the detectors 33b, 33c, and 33d.

The detectors 33b, 33c, and 33d may be each configured of a light detector such as a photodiode, and respectively detect intensity of R light, G light, and Blight that are outputted from the demultiplexer 33a. The detectors 33b, 33c, and 33d respectively generate analog R, G, and B detection signals corresponding to intensity of the detected R light, G light, and B light, and provide the respective detection signals to the A/D converters 33e, 33f, and 33g.

The A/D converters 33e, 33f, and 33g respectively convert the analog R, G, and B detection signals respectively provided from the detectors 33b, 33c, and 33d, into digital R, G, and B detection signals to provide the respective signals to an image generation section 34c that generates an image and is provided in the controller 34.

The memory 35 previously holds a control program and the like to control the main body device 3. In addition, the information of the coordinate position that is read from the memory 25 is held in the memory 35 by the controller 34 of the main body device 3.

The controller 34 is configured using a CPU or the like, reads out the control program stored by the memory 35, and controls the light source unit 31 and the driving unit 32 based on the read control program.

Figure 3B:
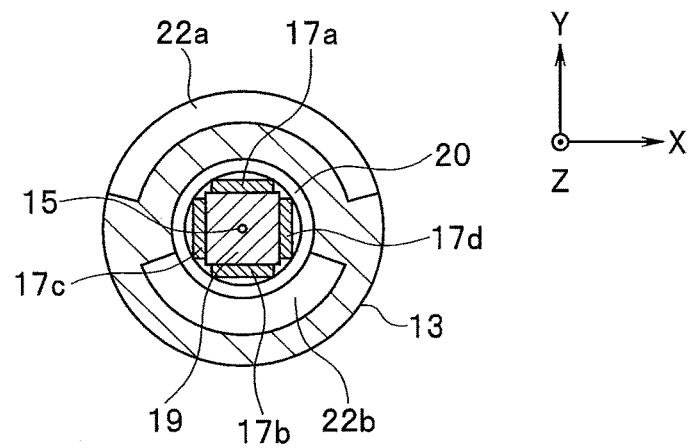
FIG. 3B is a sectional view taken along line B-B in FIG. 2.

The cutouts 22a and 22b that form the absorption part 21 are provided in the cylindrical member 13 in a spiral shape in the longitudinal direction as illustrated in FIG. 3B. FIG. 3B illustrates a cross-sectional surface taken along line B-B in FIG. 2. In the example illustrated in FIG. 2, the cutouts 22a and 22b are respectively formed on the outer circumferential face and the inner circumferential face of the cylindrical member 13 so as to have a length of about half of the circumference, for example. However, the lengths of the cutouts 22a and 22b and a distance between the cutouts 22a and 22b adjacent to each other in the longitudinal direction of the cylindrical member 13 may be changed according to the materials and the sizes of the cylindrical member 13 and the ferrule holding member 20 and characteristics of the actuator 17, and the like. In the present embodiment, a depth (a depth of a groove) d of each of the cutouts 22a and 22b is set to about half of a thickness t of the cylindrical member 13, for example, as illustrated in FIG. 3B.

Figure 3C:
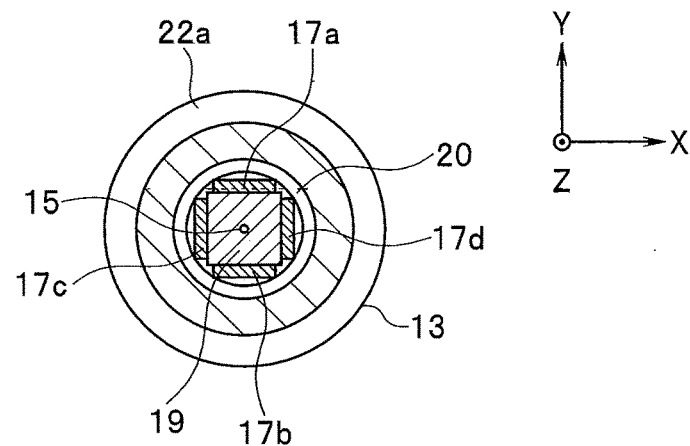
FIG. 3C is a lateral cross sectional view illustrating a ring-shaped cutout in a first modification.

Note that, in place of providing the cutouts 22a and 22b in a spiral shape as illustrated in FIG. 3B, the cutouts 22a and 22b may be provided in an annular shape in a circumferential direction as illustrated in FIG. 3C. Also, in FIG. 3C, when the cutout 22a is provided in the annular shape on the outer circumferential face, the cutout 22b is so provided on the inner circumferential face as not to overlap with the cutout 22a in order to prevent the strength of the cylindrical member 13 from being excessively lowered due to the cutout 22a provided in the annular shape.

The scanning endoscope 2 of the present embodiment includes: the optical fiber 15 that guides light emitted from the light source unit 31 forming a light source section, and emits the light from the distal end; the actuator 17 that expands and contracts in response to a provided voltage to scan with the light emitted from the distal end of the optical fiber 15; the ferrule 19 that is interposed between the optical fiber 15 and the actuator 17, and transmits, to the optical fiber 15, force corresponding to the expansion and contraction of the actuator 17; the ferrule holding member 20 forming the ferrule holding part that is connected to the ferrule 19 to hold the ferrule 19; the cylindrical member 13 forming a lens holding part that has a space containing the optical fiber 15, is formed of a cylindrical member provided outside the optical fiber 15 along the optical fiber 15, and holds the illumination lens 16 serving as a lens that receives the light emitted from the distal end of the optical fiber 15 and emits illuminating light to an object; and the absorption part 21 that is provided between the ferrule holding part and the lens holding part, and is formed of the cutouts 22a and 22b or the like that absorb or suppress vibration, in the longitudinal direction of the cylindrical member, of one or both of the ferrule holding part and the lens holding part.

Next, action of the present embodiment is described.

When the scanning endoscope 2 is connected to the main body device 3 and is put into an operation state, the controller 34 reads out the information of the memory 25 and stores the information in the memory 35. Also, the scanning control section 34b of the controller 34 controls the driving unit 32 to apply the drive signal to the actuator 17. The actuator 17 spirally moves (swings) the distal end side of the optical fiber 15 from a scanning start position Pst to a scanning end position Pen illustrated in FIG. 4B in response to the application of the drive signal.

Also, the light source control section 34a of the controller 34 controls the light source unit 31 to discretely perform pulse light emission at predetermined coordinate positions sequentially. In addition, the detection unit 33 sequentially samples the returned light from the subject 5 side in the discrete pulse emission, to acquire a detection signal. The detection unit 33 provides the acquired detection signal to the image generation section 34c, and the image generation section 34c temporarily stores the provided detection signal in, for example, the memory 35.

The image generation section 34c of the controller 34 converts image information that includes the detection signal stored in the memory 35 and the positional information of the pulse light emission at the time of acquiring the detection signal, into a standard image signal in a standard image signal of raster scan, thereby providing the image signal to the monitor 4. Then, an endoscope image is displayed on the monitor 4.

Figure 5:
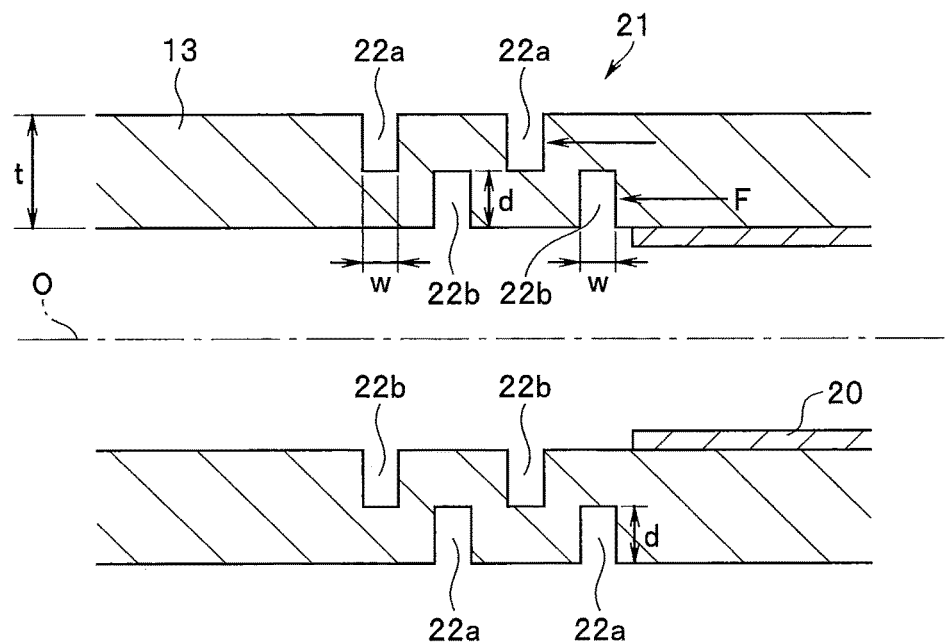
FIG. 5 is an action explanatory diagram of the embodiment.

The endoscope image displayed on the monitor 4 is acquired by swinging the distal end of the optical fiber 15 forming a light guide part in the X-axis direction and the Y-axis direction by the actuator 17 in a predetermined holding state in which the proximal end side of the actuator 17 is held in a state in which the central axis of the ferrule holding member 20 and the central axis of the optical fiber 15 is set to the central axis O of the cylindrical member 13 (see FIG. 5). The X-axis direction and the Y-axis direction are directions orthogonal to the central axis O.

When the distal end of the optical fiber 15 is moved (swung) by the actuator 17 to spirally scan in the above-described manner, it is desirable to prevent the illumination lens 16 held by (fixed to) the distal end of the cylindrical member 13 from being vibrated in order to acquire an image with high image quality.

In other words, when the distal end of the optical fiber 15 is swung (moved) by the actuator 17, the ferrule holding member 20 is also vibrated by swing of the actuator 17 because the proximal end of the ferrule 19 attached with the actuator 17 is fixed to the rear end of the cylindrical member 13 through the ferrule holding member 20. The vibration may be transferred, by the cylindrical member 13, to a part holding the illumination lens 16 the distal end side, which may vibrate the illumination lens 16.

In the present embodiment, the vibration propagated through the cylindrical member 13 in the longitudinal direction is absorbed or suppressed in the following trimmer. FIG. 5 is an enlarged view illustrating the vicinity of the absorption part in FIG. 2.

In FIG. 5, for example, when longitudinal vibration is propagated from the proximal end side of the cylindrical member 13 (right side in FIG. 5) to left side along the longitudinal direction of the cylindrical member 13 as illustrated in an arrow F, the propagation of the vibration is reduced or suppressed by the cutouts 22b and 22a as illustrated in FIG. 5. Note that propagation of the longitudinal vibration is similarly reduced or suppressed by the cutouts 22a and 22b also in the cylindrical member 13 on lower side than the central axis O of the cylindrical member 13 in FIG. 5. Since the cutouts 22a and 22b on upper side of the central axis O in FIG. 5 similarly act, action of the cutout 22b is mainly described.

When the cutout 22b is not provided, the longitudinal vibration is propagated without being largely attenuated; however, the propagation is reduced by air in the cutout 22a part at which transfer characteristics are largely different and function of transferring the longitudinal vibration is sufficiently small.

Since the cutout 22b has the depth d that is half of the thickness t of the cylindrical member 13, propagation of the vibration propagating through a part not provided with the cutout 22b is reduced or suppressed similarly by the cutout 22a that is provided adjacent to the cutout 22b (in the longitudinal direction of the cylindrical member 13). The cutouts 22b and 22a reduce the propagation of the vibration with the depth covering the thickness t, which makes it possible to effectively suppress the propagation of the longitudinal vibration.

Also, the plurality of cutouts 22a and 22b are provided in the longitudinal direction, which makes it possible to further suppress the propagation of the longitudinal vibration as compared with a case in which the cutouts 22a and 22b are singularly provided.

Providing the plurality of cutouts 22a and 22b at positions in the cylindrical member 13 close to the ferrule holding member 20, which allows for effective suppression (reduction) of the vibration unnecessarily vibrating the illumination lens 16 side, in the vicinity of the vibration generation source.

Note that a value of a width (a cutout width) w of each of the cutouts 22a and 22b in the longitudinal direction of the cylindrical member 13 illustrated in FIG. 5 may be set in the following manner. It is known that propagation velocity Vc of the longitudinal vibration (or a vertical wave) propagating through a medium that forms the rigid cylindrical member 13 and transfers the longitudinal vibration, such as stainless steel, is expressed by the following equation (1), $$Vc = (K/\rho) \tag{1}$$

where K is a bulk modules of the medium, and $\rho$ is density.

In contrast, in a case of the air in the cutouts 22a and 22b, it is known that propagation velocity Va of the longitudinal vibration at the air part in the cutouts 22a and 22b is represented by the following equation (2), $$Va = (\gamma p/\rho)^{1/2} \tag{2}$$

where p is pressure, V is volume, and $\gamma$ is a ratio of specific heat at constant pressure and specific heat at constant volume. The propagation velocity Va in the air may be an order of about one-tenth of the propagation velocity Vc in the case of a metal such as stainless steel. Thus, when it is assumed that longitudinal vibration occurs at a frequency f of vibration that swings the optical fiber 15 in the X direction or the Y direction, for example, a phase of the longitudinal vibration that propagates through the part not provided with the cutout 22a by the cutout width w is largely varied (With an order of about ten times) whereas the phase variation in the case where the longitudinal vibration propagates via the cutout 22a with small cutout width w is small.

With use of the phenomenon, the cutout width w of each of the cutouts 22a and 22b may be set to half or (n+½) times, where n is a natural number, of the wavelength $\lambda$ of the longitudinal vibration with the frequency f propagating through the cylindrical member 13 not provided with the cutouts 22a and 22b. Note that the cutout width w may be set in consideration of (small) phase variation at the cutouts 22a and 22b.

The cutout width w is set such that the longitudinal vibration propagating via the part provided with the cutouts 22a and 22b and predetermined longitudinal vibration propagating via the part not provided with the cutouts 22a and 22b are composed (added) with substantially inverted phases, as mentioned above. This makes it possible to effectively suppress or absorb the longitudinal vibration propagating through the cylindrical member 13 in the longitudinal direction.

For example, when the cutout width w is set such that a phase difference becomes ½ of the wavelength of the longitudinal vibration at the predetermined frequency f, the propagation of the longitudinal vibration is expected to be effectively suppressed with small cutout width w.

In the above-described case, the action to reduce, by the cutouts 22a and 22b, the longitudinal vibration propagating through the cylindrical member 13 in the longitudinal direction is described. When the cutout width w is so set as to add vibration with the inverted phases as mentioned above, an effect of further suppressing the propagation is exerted with respect to the predetermined longitudinal vibration.

When specific longitudinal vibration propagating through the part provided with the cutouts 22a and 22b and specific longitudinal vibration propagating through the part not provided with the cutouts 22a and 22b are composed with inverted phases, a value of the depth d of each of the cutouts 22a and 22b may be set to a value larger than the half of the thickness t.

Figure 6:
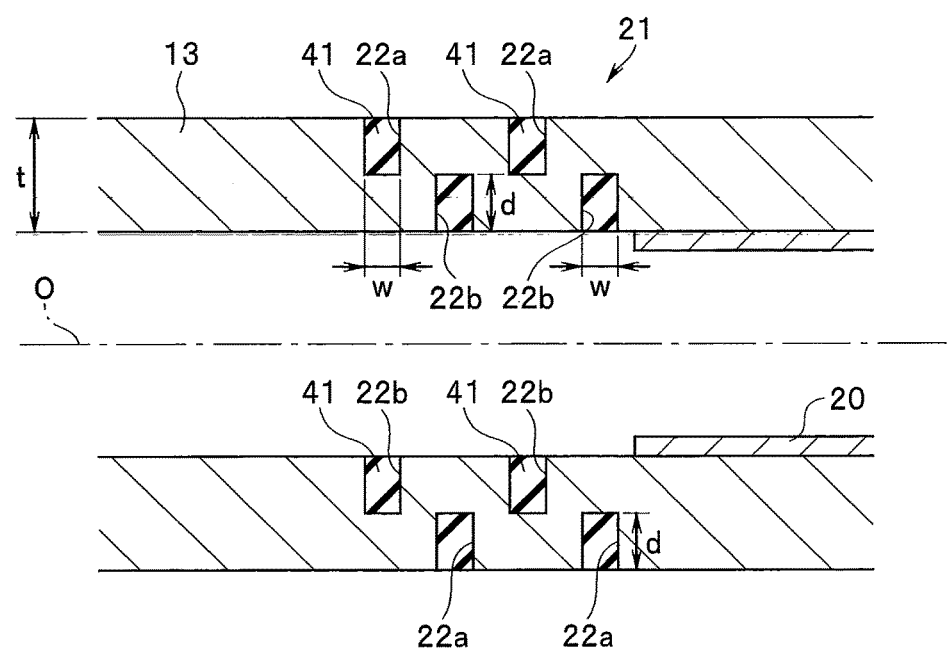
FIG. 6 is a longitudinal sectional view illustrating a configuration near an absorption part in a second modification of the embodiment.

In the above-described embodiment, the case where the cutouts 22a and 22b are provided has been described. Alternatively, the cutouts 22a and 22b may be filled with a vibration absorbing member 41 such as a rubber that has property to absorb or attenuate vibration, as with a second modification illustrated in FIG. 6. Note that FIG. 6 illustrates a configuration in which each of the cutouts 22a and 22b in FIG. 5 is filled with the vibration absorbing member 41, and other components are similar to those in the above-described embodiment.

In the present modification, the longitudinal vibration propagating in the cutouts 22a and 22b are effectively absorbed or attenuated by the vibration absorbing member 41.

Figure 7:
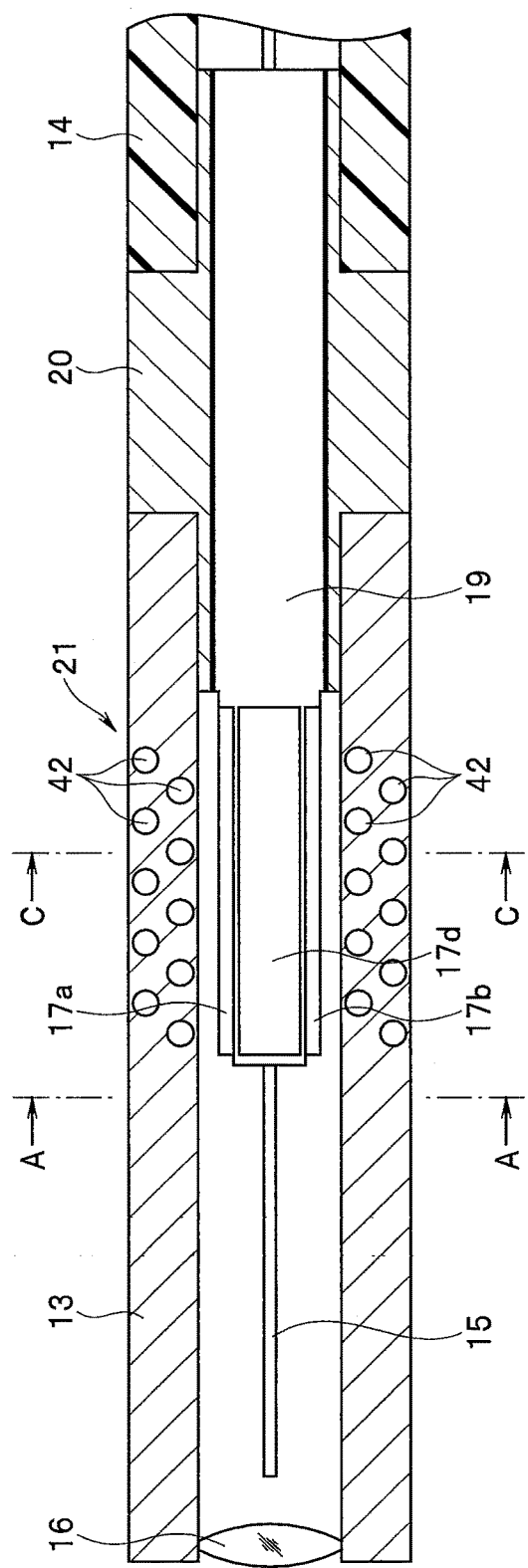
FIG. 7 is a longitudinal sectional view illustrating a configuration inside a cylindrical member of a scanning endoscope of a third modification of the embodiment.

Next, a third modification of the present invention is described. FIG. 7 illustrates a configuration inside a cylindrical member in a scanning endoscope of the third modification.

In the present modification, the absorption part 21 in the cylindrical member 13 illustrated in FIG. 2 is formed of, in place of the cutouts 22a and 22b, a plurality of holes 42 each having a space of a spherical shape or other shape.

Figure 8:
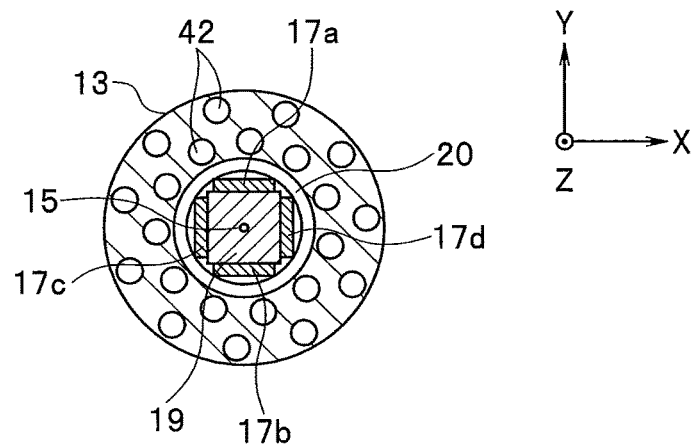
FIG. 8 is a sectional view taken along line C-C in FIG. 7.

The plurality of holes 42 are each smaller in size than the thickness t of the cylindrical member 13, and are irregularly or regularly provided in the cylindrical member 13 on side closer to the ferrule holding member 20. Note that a cross-sectional surface taken along line A-A in FIG. 7 is the same as that in FIG. 3A. Also, a cross-sectional surface taken along line C-C in FIG. 7 is as illustrated in FIG. 8.

Figure 9:
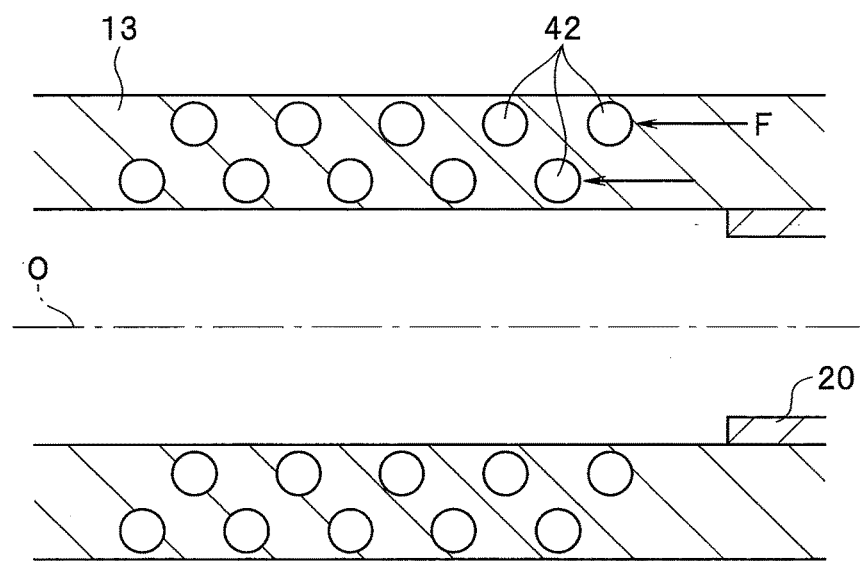
FIG. 9 is an action explanatory diagram of the third modification.

FIG. 9 illustrates an action explanatory diagram of the present modification. The action of the present modification is similar to that in the case of FIG. 5. The longitudinal vibration propagating from the right side of the cylindrical member 13 as illustrated in an arrow F is sufficiently attenuated by the holes 42. The longitudinal vibration that has propagated through a part not provided with the holes 42 is sufficiently attenuated by the plurality of holes 42 disposed along the longitudinal direction of the cylindrical member 13. Therefore, effects substantially similar to those in the above-described embodiment are exerted.

An embodiment configured by partially combining the above-described embodiment and the like is also incorporated in the present invention.

What is claimed is:

1. A scanning endoscope, comprising:
   an optical fiber that guides light emitted from a light source section, and emits the light from a distal end;
   an actuator that expands and contracts in response to a provided voltage to scan with the light emitted from the distal end of the optical fiber;
   a ferrule that is interposed between the optical fiber and the actuator, and transmits, to the optical fiber, force corresponding to the expansion and contraction of the actuator;
   a ferrule holding part that is connected to the ferrule to hold the ferrule;
   a lens holding part that has a space containing the optical fiber, is formed of a cylindrical member provided outside the optical fiber along the optical fiber, and holds a lens, the lens receiving the light emitted from the distal end of the optical fiber and emitting illuminating light to an object; and
   an absorption part that is provided between the ferrule holding part and the lens holding part, and absorbs vibration, in a longitudinal direction of the cylindrical member, of at least one of the ferrule holding part and the lens holding part.

2. The scanning endoscope according to claim 1, wherein the absorption part is provided at a position closer to the ferrule holding part than the lens held by the lens holding part.

3. The scanning endoscope according to claim 1, wherein the absorption part is formed of a plurality of holes each having a size smaller than a thickness of the cylindrical member, at a middle part of the cylindrical member in the longitudinal direction.

4. The scanning endoscope according to claim 1, wherein the absorption part is formed of a plurality of cutouts at a middle part of the cylindrical member in the longitudinal direction.

5. The scanning endoscope according to claim 1, wherein the absorption part is formed to include a first cutout that is formed in a ring shape along a circumferential direction from outer circumferential face side of the cylindrical member and a second cutout that is formed in a ring shape along a circumferential direction from inner circumferential face side of the cylindrical member, at a middle part of the cylindrical member in the longitudinal direction.

6. The scanning endoscope according to claim 1, wherein the absorption part is formed to include a first cutout that is formed in a ring shape with a depth of about half of a thickness of the cylindrical member along a circumferential direction from outer circumferential face side of the cylindrical member and a second cutout that is formed in a ring shape with a depth of about half of the thickness of the cylindrical member along a circumferential direction from inner circumferential face side of the cylindrical member, at a middle part of the cylindrical member in the longitudinal direction.

7. The scanning endoscope according to claim 4, wherein a value of a cutout width of the cylindrical member in the longitudinal direction is set to allow, with respect to longitudinal vibration that propagates through the cylindrical member in the longitudinal direction and vibrates with a frequency equivalent to a predetermined frequency at which the actuator is driven, a phase of the longitudinal vibration that propagates through the cutout by the cutout width to be substantially inverse to a phase of the longitudinal vibration that propagates, by the cutout width, through a part of the cylindrical member not provided with the cutout.

8. The scanning endoscope according to claim 4, wherein the absorption part is formed by filling each of the plurality of cutouts with a vibration absorbing member that absorbs the vibration.

\* \* \* \* \*